United States Patent [19]

Murray

[11] Patent Number: 4,551,863
[45] Date of Patent: Nov. 12, 1985

[54] FEMORAL COMPONENT AND METHOD

[76] Inventor: William M. Murray, 145 Bryce Rd., Camp Hill, Pa. 17011

[21] Appl. No.: 698,272

[22] Filed: Feb. 4, 1985

Related U.S. Application Data

[63] Continuation of Ser. No. 305,914, Sep. 28, 1981, abandoned.

[51] Int. Cl.[4] .................................................. A61F 1/04
[52] U.S. Cl. ...................................................... 623/23
[58] Field of Search ........................ 3/1.9, 1.91, 1.911, 3/1.912, 1.913; 128/92 C, 92 CA

[56] References Cited

U.S. PATENT DOCUMENTS

| | | | |
|---|---|---|---|
| 3,658,056 | 4/1972 | Huggler et al. | 128/92 CA |
| 3,871,031 | 3/1975 | Boutin | 3/1 |
| 3,938,198 | 2/1976 | Kahn et al. | 3/1.9 |
| 3,939,497 | 2/1976 | Heimke et al. | 3/1.912 |
| 3,979,779 | 9/1976 | Zeibig et al. | 3/1.9 |
| 3,987,499 | 10/1976 | Scharbach et al. | 128/92 C |
| 4,004,581 | 1/1977 | Heimke et al. | 3/1.912 |
| 4,021,864 | 5/1977 | Waugh | 3/1.91 |
| 4,038,703 | 8/1977 | Bokros | 3/1.9 |
| 4,051,559 | 10/1977 | Pifferi | 3/1 |
| 4,129,903 | 12/1978 | Huggler | 3/1 |
| 4,187,559 | 2/1980 | Grell et al. | 3/1.91 |
| 4,272,855 | 6/1981 | Frey | 3/1.9 |
| 4,306,550 | 12/1981 | Forte | 128/92 E |
| 4,459,708 | 7/1984 | Buttazzoni | 128/92 CA |

FOREIGN PATENT DOCUMENTS

| | | | |
|---|---|---|---|
| 2318396 | 10/1974 | Fed. Rep. of Germany | 3/1.912 |
| 2621666 | 11/1977 | Fed. Rep. of Germany | 3/1.91 |
| 2839093 | 3/1980 | Fed. Rep. of Germany | 3/1.911 |
| 2052999 | 2/1981 | United Kingdom | 3/1.912 |

OTHER PUBLICATIONS

Dana C. Mears, Materials and Orthopaedic Surgery, 1979, pp. 523–531.

Primary Examiner—Richard J. Apley
Assistant Examiner—David J. Isabella
Attorney, Agent, or Firm—Thomas Hooker

[57] ABSTRACT

An implant component having a cement stem, a shaft extending outwardly of the proximal end of the stem and a head fitted on the shaft including a bone joint ball and bone ingrowth material on the neck of the head. The component is secured to the proximal end of a live femur by cementing the stem into the medullary canal, positioning the surface of the ingrowth material flush against a complementary live bone surface and growing a live bone connection into the ingrowth material.

13 Claims, 13 Drawing Figures

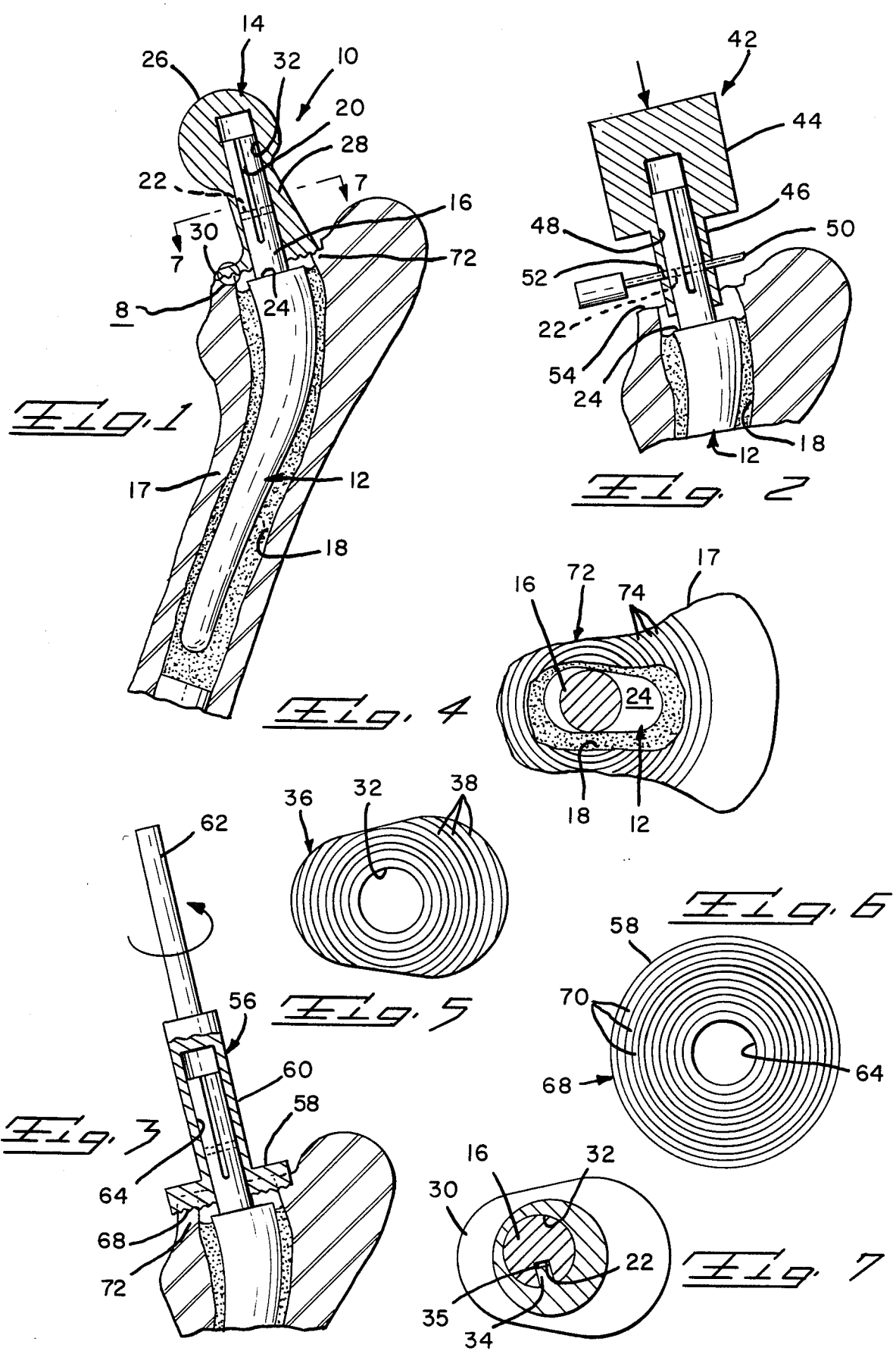

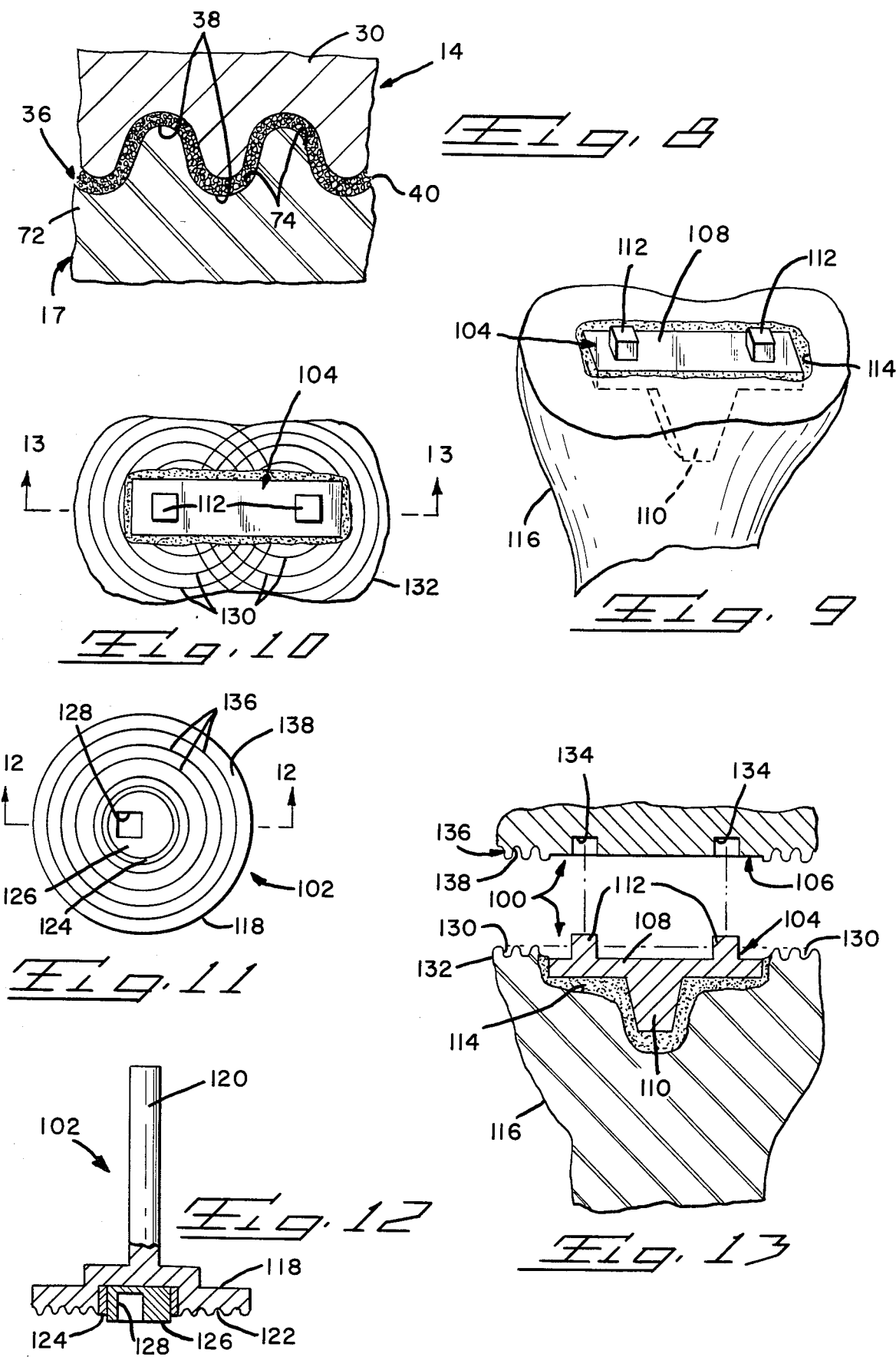

FEMORAL COMPONENT AND METHOD

This application is a continuation of my co-pending application for "Femoral Component and Method", Ser. No. 305,914 filed Sept. 28, 1981 abandoned.

This invention relates to orthopedic bone implant components, particularly to implants carrying joint members. These members are intended to be permanently attached to live bones to replace natural joint members. The invention also relates to methods for securing the components to live bone. The invention may be used to secure a prosthetic hip joint ball to a femur.

Conventional bone implant components are secured to live bones by forming the cavity in the bone, filling the cavity with bone cement and then inserting a component stem into the cement to form a connection between the stem and the surrounding bone. Problems are experienced with this type of connection. The connection tends to weaken in time. The rigid component extends as a cantilever out of the cavity so that axial and lateral forces applied to the free end or head are transmitted directly to the stem-cement-bone connection. Loading of the cement connection, commonly weakened by ostioporosis and naturally forming interposition membrane may loosen the stem and, in some cases fracture the stem. Osteoporosis or bone absorption occurs at the mouth of the cavity where the live bone is not stressed. Bone absorption loosens the cement connection at the proximal end of the stem while the distal end remains firmly cemented to the bone. In this situation, repetitive bending or lateral forces exerted on the stem are transmitted along the stem to the bone at the anchored distal end and the stem is bent back and forth about the anchored end in response to the forces. A stem bent in this manner may become fatigued and fracture immediately above the anchored distal end.

The present invention is a orthopedic bone implant component and method for improving the strength and permanency of the connection between live bone and the component by the use of a stem cemented with a cavity in the live bone and a head or mounted member attached to the permanently secured stem by a sliding connection with a surface on the mounted member carrying a bone surface meshed with similarly shaped surface formed on the proximal end of the bone. Axial forces exerted on the head or mounted member are transmitted directly across the surface to the bone. Such axial loading of the proximal end of the bone, remote from the stem, shields the stem from forces which tend to loosen it and biases the head or mounted member directly against the bone to promote intergrowth of the bone across the surface and into the head, further improving the strength of the bond between the bone and the head. The surface at the interface between the bone and head may have a large area hill and valley shape, thereby increasing the strength of the bond between the two. The height of the meshed hills and valleys locks the head to the bone and aids in resolving lateral stresses remote from the cemented stem. A keyed connection between the stem and head prevents rotation of the head on the stem until the bone has grown into the implant material to secure the head in place of the bone.

The resolution of forces transmitted to the head at the hill and valley surface assures that the proximal end of the bone is subjected to stresses approximating normal physiological stresses. This stressing of the bone prevents osteoporosis and promotes the formation of a strong intergrowth of bone within the bone implant material on the surface of the head.

The invention enables a head carrying an orthopedic component to be secured to a stem permanently cemented to live bone with a surface of the head closely conforming to a surface of the bone adjacent the stem. The close conformity of the surfaces is obtained by shaping the bone using a tool mounted on the stem and having a surface conforming to the surface of the head.

Stressing the proximal end of a bone carrying an orthopedic applicance is broadly disclosed in Grell et al U.S. Pat. No. 4,187,559. This patent discloses a bulky femoral prosthesis having a stem anchored within the medullary canal and a hip joint ball pivotally mounted on the stem about an axis to one side of the stem so that the flat lower surface of the ball rests on the calcar. Forces transmitted to the ball pivot it down against the calcar. Lateral forces are undesirably transmitted to the stem.

Other objects and features of the invention will become apparent as the description proceeds, especially when taken in conjunction with the accompanying drawings illustrating the invention, of which there are two sheets and two embodiments.

IN THE DRAWINGS

FIG. 1 is a sectional view illustrating the component implanted in a femur;

FIG. 2 is a sectional view illustrating the method by which the component stem is implanted within the femoral medullary canal;

FIG. 3 is a sectional view illustrating shaping the exposed proximal end of the femoral shaft;

FIG. 4 is a top view illustrating the shaped proximal end of the femoral shaft;

FIG. 5 is an end view of the component head illustrating the complementary surface which engages the shaped end of the femoral shaft;

FIG. 6 is an end view of the tool used to shape the proximal end of the femoral shaft;

FIGS. 7 and 8 are enlarged sectional views taken at line 7—7 and area 8 of FIG. 1, respectively;

FIG. 9 is a perspective view of the stem of a second embodiment component cemented to a bone;

FIG. 10 is a top view of the stem and surface of the bone shown in FIG. 9 afer shaping.

FIG. 11 is an end view of the tool used in shaping the bone of FIG. 9

FIG. 12 is a sectional view taken partially along line 12—12 of FIG. 11; and

FIG. 13 is a sectional view illustrating attachment of a component to the stem and bone shown in FIG. 9.

FIRST EMBODIMENT OF THE INVENTION

The first embodiment of the invention, as illustrated in FIGS. 1 through 8 relates to a femoral component 10 including femoral stem 12 and head 14. The head is mounted on the end of a cylindrical shaft 16 extending outwardly from the stem.

The component 10 is secured to the proximal end of femur 17 following amputation of the natural femoral head. Stem 12 is cemented within the femoral medullary canal 18 in a conventional manner as indicated in FIG. 1. The stem may be of conventional design. Shaft 16 extending outwardly from the stem includes a longitudinal keyway 20 extending along one side from the free end of the shaft toward the stem. A diametral cross bore 22 extends through the shaft approximately midway between shoulder 24 at the end of the stem and the free end of the shaft.

Component head 14 includes a spherical ball 26 and a neck 28 having a lip 30 extending partially around one side of the neck. A cylindrical bore 32 extends from the end of the neck into the ball 26. Key 34 extends into bore 32 and runs a distance along the length of the bore. See FIG. 7. The shaft 16 has a close sliding fit within the bore with key 34 in keyway 20 to prevent rotation of the head on the shaft. The depth of the keyway is slightly greater than the height of the key to provide a passage 34 extending past the key and communicating the ends of the keyway.

The lower surface 36 of head 14 is shown in FIG. 5. The surface extends across the ends of the neck 28 and lip 30 and includes a series of smooth circular hills and valleys concentric with the bore 32. Surface 36 is perpendicular to the axis of the bore with the hills and valleys 58 extending radially outwardly of the bore. As shown in FIG. 8, the surface 36 is defined by a porous layer of bone implant material 40 fixedly secured to the head 14. This material may be made of sintered metal balls or other bone implant material which promotes the growth of living bone into the cavities within material 40. As shown in FIG. 5, the lower surface of the head 14 is not circular so that some of the hills and valleys are discontinuous at the sides of the surface.

The femoral component 10 is implanted within the proximal femoral shaft by first amputating the live femoral head and preparing the medullary canel to be filled with bone cement. After the canal has been filled with cement, femoral stem 12 is inserted into the canal by using an implanting tool 42 shown in FIG. 2. Tool 42 includes a handle 44 and circular collar 46. Bore 48 extends from the free end of the collar into the handle. The bore has a close sliding fit on stem shaft 16.

Prior to inserting the femoral stem 12 into the prepared and filled medullary canal 18, the implanting tool 42 is mounted on stem shaft 16 and locking pin 50 in extending through a cross bore 52 in the collar 46 and the cross bore 22 in the shaft to rigidly secure the tool to the femoral stem. The femoral stem is then accurately positioned within the filled medullary canal by appropriate manipulation of the tool 42. Proper positioning of the stem within the canal may require movement of the end collar 46 into the open end of the canal 18. The outside diameter of collar 46 is less than the spacing between the inner walls of the medullary canal to permit free entry of the collar into the canal. The stem is properly seated within the canal when shoulder 24 is located a distance below surface 54 at the end of the canal.

After the stem has been properly positioned as illustrated in FIG. 2, pin 50 is withdrawn and tool 42 is removed from the stem. The surface 54 and end of the medullary canal at shoulder 24 are cleaned to remove excess bone cement and debris. The cement holding the stem to the femoral shaft is then allowed to harden in order to secure the stem to the bone.

After the cement has hardened, a calcar surfacing tool 56 is positioned on the shaft 16 as shown in FIG. 3. Tool 56 includes a work heard 58, body 60 extending from one side of the head and an axial shaft 62 extending from the body. The body and shaft are coaxial with head 58. Axial bore 64 extends through head 58 and into body 60. The shaft 16 has a close sliding fit within bore 64. The lower surface 68 of head 58, facing away from shaft 62 is provided with a series of abrasive bone-shaping hills and valley 70 having the same shape and radius as the hills and valleys 38 on head surface 36. Rotation of tool 56 on shaft 16 by a rotary driver device (not illustrated) sweeps the shaping hills and valleys 70 over the bone at the end 54 of the cortical shaft and levels the end of the cortical shaft to form a surface perpendicular to the axis of shaft 16 with valleys and hills formed in the live bone complementary with the hills and valleys of tool 56. Bore 64 is sufficiently deep to allow the tool to be fed axially along pin 16 toward shoulder 24 to thereby assure all of the cortical shaft beneath the work head is shaped to the desired planar valley and hill configuration. FIG. 4 illustrates the formed end 72 of the cortical shaft with a series of circular valleys and hills 74 concentric with the axis of shaft 16.

Following formation of the valleys and hills 74 on the end of the cortical shaft 72, as illustrated in FIG. 4, tool 56 is withdrawn from shaft 16 and the end of the femur is again cleaned to remove bone fragments and any other debris from the surfacing operation. Head 14 is then mounted on the femoral stem 12 by extending bore 32 over the stem shaft 16 with key 34 fitted in keyway 20. The resultant slot-and-groove connection prevents rotation of the head with respect to the shaft while permitting longitudinal axial movement of the head with respect to the shaft. The head is slid down the shaft so that the hills and valleys 38 on lower surface 36 fit together in surface-to-surface engagement with complementary valleys and hills 74 formed on the end of the cortical shaft 72, as illustrated in FIG. 8. The outer surface of the sintered metal bone implant layer 40 abuts flush on the valley and hill surface 74 formed in the live bone at the end of the medullary canal. During insertion of the head on the shaft 16, fluid and air trapped within bore 32 escape through keyway passage 35.

After mounting of the head on shaft 16 the operative procedure is completed by seating ball 26 within a previously implanted prosthetic acetabulum socket and closing the soft tissue incisions in a conventional manner.

Forces applied to the head 14 through the hip joint are predominantly compressive, that is, parallel to the axis of shaft 16 and bias the head against the live bone 72 at the end of the cortical shaft. Forces parallel to the axis of shaft 16 are not transmitted to stem 12 because of the sliding fit between the head and stem. These axial forces are transmitted directly to the live bone end of the cortical shaft to expose the live bone to stresses similar to the stresses experienced naturally. Such stressing promotes active bone growth and avoids the calcar resorption common in conventional femoral prostheses which do not transmit stress to the proximal end of the cortical shaft.

The bone 72 at the formed end of the cortical shaft grows into the interstices of the implant surface 40 to form a strong connection between the head and the bone. The strength of the bony ingrowth connection between the femur and head 14 is believed to equal or exceed the strength of the stem-cement-bone connection in the medullary canel, particularly when a conventional interposition membrane forms at the connection between the cement and the interior walls of the medullary canal. The strong connection between the femur and the head 14 shields the connection between the lower portion of stem 12 and the cortical shaft from lateral loading to reduce the possibility of stem fracture or loosening.

The key-and-slot connection between the head and stem and the implant connection between the head and bone prevent rotation of the head with respect to the stem to assure all hip joint rotation occurs at the ball-acetabulum interface. The key-and-slot connection holds the head in place until the bone grows into the implant material.

The hill and valley interface between the head and live femoral bone increases the area of contact over a flat planar interface to assure a strong, large area for bone intergrowth into the implant surface 40. The complementary hill and valley surfaces also prevent later shifting of the head on the femur such as may occur due to imperfect cementing of the stem within the medullary canal, loosening of the stem or play in the connection between the stem and head. The free axial movement of the head on the shaft 16 assures that the axial loading of the head through the hip joint forces the head against the bone with the advantages previously described.

Non-axial or lateral loading of the head is largely resolved by the strong meshed hill and valley interface between the head and femur to reduce loading on the cemented connection between the stems and femur. Such lateral loading stresses the bone at the interface simulating natural hip joint stresses to promote bone growth and avoid osteoporosis at the femoral neck.

Femoral component 10 may be removed from the femur 17 by operatively disassociating the head from the end 72 of the cortical shaft, and then removing the head from the stem. With removal of the head, the end of the cortical shaft is exposed and the cemented stem may be removed more easily than in the case of conventional one-piece heads and stems.

SECOND EMBODIMENT OF THE INVENTION

Bone component 100 and associated bone-surfacing tool 102 of the second embodiment are illustrated in FIGS. 9 through 13. The component includes a mounting member or stem 104 and a mounted member or head 106 adapted to be secured to mounting member 104 and joined to the bone supporting the mounting member by a bone ingrowth connection similar to the hill and valley connection between head 14 and the bone end 72 of the first embodiment of the invention.

The mounting member or stem 104 is preferably formed from metal and includes a body 108 with a stem element 110 projecting from one side of the body and a pair of spaced square shafts 112 projecting outwardly from the other side of the body.

As illustrated in FIGS. 9 and 13, the mounting member or stem 104 is cemented into a recess 114 formed in the surface of live bone 116. The bone surrounding the member 104 projects outwardly beyond body 108. After the cement securing the mounting member or stem 104 to bone 116 has set, tool 102 is mounted on one square shaft 112 to form overlapping circles of hills and valleys on the end surface of bone 116. The tool 102 is similar to tool 56 and includes a work head 118, shaft 120 extending from the head. The lower end of the head includes a series of circular hills and valleys concentric with the axis of shaft 120 formed of bone surfacing material, similar to the lower surface of tool 56. The lower surface of tool 102 includes a bearing 124 and a center member 126 connected to the work head 118 throught bearing 124. Off axis square bore 128 extends into the center member 126.

Tool 102 is fitted on mounting member or stem 104 by piloting square bore 128 over one of the square shafts 112 to secure the center member 126 in a fixed position with respect to the end of bone 116. The center member may be mounted on the square shaft in four positions with the axis of tool 102 positioned differently on the bone 106 in each position. In practice, the surgeon selects the position which locates the tool axis preferentially for forming continuous, strong hills and valleys in the bone. Tool 120 is fitted in a rotating device (not illustrated) and the rotating device is actuated to rotate the tool on a lower surface to cut a series of concentric round hills and valleys 130 in the surface of bone 116 adjacent the shaft 112. The hills and valleys are preferably cut into the bone to a depth until center member 126 bottoms on body 108. Following bottoming of the tool on the first shaft 112, the tool is removed from the shaft and is optimally positioned on the second shaft and the bone surrounding the second shaft is cut to form hills and valleys 130 until the center member 126 bottoms once more on body 108. Again, the hills and valleys are cut until the member 26 bottom on body 108. The upper surface body 108 is planar and shafts 112 extends perpendicularly outwardly from the surface so that the cut hills and valleys surround the two square shafts 112 lie on the same flat surface perpendicular to the axes of the shafts. As illustrated in FIG. 10, the hills and valleys preferably cover the entire end surface 132 of bone 115 and intersect each other between the shafts.

The mounted member or head 106 is preferably formed of metal and includes a pair of spaced square bores 134 adapted to fit over post 102 and two surrounding series of concentric hills and valleys 136 defined by a layer of bone implant surface material 138 identical to the sintered surface material 40 on the hills and valleys of head 14.

Following formation of the hills and valleys 130 in bone 116, the end of the bone is cleaned of debris and the mounted member or head 106 is positioned on the end of the bone by moving the bores 134 over the square posts 112. The hills and valleys 138 of head 106 fits snugly into the valleys and hills 130 formed in bone 116 in the same way as illustrated in FIG. 8. When mounted on bone 116, the mounted member or head 106 is spaced away from the body 108 of mounting member or stem 104 to assure that forces parallel to the axes of parts 112 are transmitted directly to the bone through the intimate hill and valley connection. The live bone at end 132 grows into the interstices of material 138 thereby forming a secure connection between the bone and the mounted member or head 106 along the large area of interface between the two. The hill and valley connection of the second embodiment has the advantages of the hill and valley connection of the first embodiment.

Both embodiments disclose forming sinusoidally shaped hills and valleys in circles in the end of the bone so as to mesh with complementary shaped valleys and hills formed in the sintered surface on the mounted member or head. I contemplate that other shapes and patterns of meshing hills and valleys may be used if desired. The shape of the hills and valleys need not be sinusoidal. In some applications, the hills and valleys may extend straight along but not surround the mounting shaft or shafts. Additionally, the hill and valley surface need not be flat perpendicularly to the axis of the shaft or shafts as long as the complementary hill and valley surfaces intermesh to promote bone growth and to absorb axial loading forces.

Typically, the mounted member or head 106 of the second embodiment carries a bone joint element or other prosthetic orthopedic device. For example, the bone component 100 may be used to secure a bone to one member of a knee, wrist or ankle joint.

The shaft may extend from the head and the bore may extend into the stem with a keyed sliding connection provided as in the first embodiment. This type of connection would function equivalently to the keyed shaft and bore connection as illustrated and described.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim my invention is:

1. A femoral implant component comprising:
   a. a stem element including an elongate cement stem adapted to be cemented into a prepared medullary canal at the proximal end of a live femur, and a shaft on the cement stem extending beyond the proximal end of the cement stem, the cement stem including a distal end to be positioned within the canal, a proximal end to be positioned adjacent the proximal end of the canal, and a cement contact surface surrounding the cement stem between the distal and proximal ends for forming a bond with bone cement in the canal; and
   b. a head element mounted on the stem element including a spherical bone joint ball away from the cement stem, a neck on the side of the ball toward the cement stem, a bore extending into the end of the neck toward the ball, and a layer of porous bone ingrowth material on the surface of the neck to lie against resected surface of the femur, the shaft extending into the bore so that the end of the neck surrounds the shaft and is adjacent to the proximal end of the cement stem, the head and stem elements including anti-rotation means preventing rotation of the head element on the shaft;
   c. whereby upon implantation of the component in a live femur with the cement stem secured in the medullary canal by a cement connection and the surface of the ingrowth material lying flush against a complementary live bone surface on the proximal end of the femur the cement forms an immediate strong anchorage joining the stem element to the femur and supporting the head element with respect to the complementary surface during growth of live bone into the ingrowth material to form a long term ingrowth anchorage at the head element.

2. A femoral implant component as in claim 1 wherein the shaft and bore are complementary in shape so that the shaft orients the head component with respect to the cement stem for accurate location of the surface of the ingrowth material with respect to the cement stem.

3. A femoral implant component as in claim 2 wherein the shaft and bore are both cylindrical in shape.

4. A femoral implant component as in claim 1 wherein at least part of the surface of the ingrowth material is symmetrical with respect to the axis of the shaft to permit such part to rest flush on a live bone surface formed by moving a bone cutting tool with respect to the shaft.

5. A femoral implant component as in claim 4 wherein part of the ingrowth surface faces toward the cement stem.

6. A femoral implant component as in claim 4 wherein said part of the ingrowth surface also faces outwardly from the shaft.

7. A femoral implant component as in claim 4 wherein the shaft is smaller in transverse cross section than the proximal end of the cement stem and extends outwardly from the center of the cement stem.

8. A femoral implant component as in claim 7 including a shoulder at the proximal end of the cement stem, the transverse cross section of the cement stem increasing in circumference from the distal end to the shoulder.

9. The method of attaching an orthopaedic component to the proximal end of a live femur, the component including a stem component having a cement stem, and a shaft on the proximal end of the cement stem extending outwardly of the cement stem and a head element having a spherical hip joint ball, a neck to one side of the ball, a bore extending into the neck to receive the shaft, and a layer of porous bone ingrowth material on the surface of the neck to lie against a resected surface of the femur, using a bone shaping tool having a bore and a bone shaping face movable to form a live bone surface matching the surface of the bone ingrowth material on the head; comprising the steps of:
   a. amputating the natural femoral head from the proximal end of the femur;
   b. preparing the exposed medullary canal to accomodate the cement stem;
   c. cementing the cement stem in the prepared medullary canal with the cement stem located within the canal and the shaft extending outwardly of the canal and surrounded by live bone to form a weight bearing cement connection between the cement stem and the femur;
   d. shaping the live bone at the proximal end of the femur to a surface complementary with the surface of the bone ingrowth material on the neck by fitting the tool bore over the shaft, moving the tool with respect to the shaft to bring the shaping face into contact with adjacent live bone and shape the live bone to form the complementary surface, and then removing the tool from the shaft;
   e. mounting the head component on the shaft by fitting the head bore over the shaft and moving the head distally toward the cement stem a distance sufficient to position the surface of the ingrowth material on the neck flush against the complementarily shaped live bone surface at the proximal end of the femur and securing the head against rotation with respect to the shaft; and
   f. maintaining the cement connection between the cement stem and the femur and the flush contact between the ingrowth material and the shaped live bone surface at the proximal end of the femur while at the same time growing live femoral bone across the flush surface contact and into the interstices of the ingrowth material on the neck to form a strong ingrowth connection between the head component and the proximal end of the femur.

10. The method of claim 9 including the step of rotating the bone surfacing tool around the shaft to shape the live bone at the proximal end of the femur.

11. The method of claim 9 including the step of forming a surface in the live bone at the proximal end of the femur symmetrical around the axis of the shaft.

12. The method of claim 11 including the step of cementing the cement stem within the medullary canal below the proximal end of the femur so that the shaft joins the cement stem within the medullary canal and shaping the complementary surface on the live bone at the proximal end of the canal outwardly of the cement stem.

13. An orthopaedic system including an orthopaedic component, live femur and cement and live bone ingrowth connections joining the component and femur produced by the method of claim 9.

* * * * *